United States Patent
Tepic et al.

(10) Patent No.: US 6,409,768 B1
(45) Date of Patent: Jun. 25, 2002

(54) SCREW ANCHORED JOINT PROSTHESIS

(76) Inventors: Slobodan Tepic, Rigistrasse 27 B, Zurich (CH), CH-8006; W. Andrew Hodge, 8260 Native Dancer Rd. E., Palm Beach Gardens, FL (US) 33418

( * ) Notice: Subject to any disclaimer, the term of this patent is extended or adjusted under 35 U.S.C. 154(b) by 0 days.

(21) Appl. No.: 09/527,319

(22) Filed: Mar. 16, 2000

(51) Int. Cl.[7] ................................................. A61F 2/32
(52) U.S. Cl. ................... 623/23.27; 606/64; 623/21.11
(58) Field of Search ............................ 623/16.11, 23.44, 623/23.15, 23.26, 23.27, 21.11; 606/62, 64, 72, 73

(56) References Cited

U.S. PATENT DOCUMENTS

| | | | |
|---|---|---|---|
| 4,622,959 A | 11/1986 | Marcus | 128/92 |
| 5,053,036 A | 10/1991 | Tepic et al. | 606/69 |
| 5,151,103 A | 9/1992 | Tepic et al. | 606/69 |
| 5,458,654 A | 10/1995 | Tepic | 623/23 |
| 5,501,684 A | 3/1996 | Schlapfer et al. | 606/73 |
| 5,709,686 A | 1/1998 | Talos et al. | 606/69 |

Primary Examiner—David J. Isabella
(74) Attorney, Agent, or Firm—Pennie & Edmonds LLP

(57) ABSTRACT

Screw-based primary fixation of the prosthetic components within the medullary cavity solves the problem of micro-movements encountered in conventional press-fit cementless fixation. For a total hip prosthesis, the stem is fixed to the medial cortex of the proximal femur by the medial approach alone, obviating the need for drilling of the lateral cortex. The stem may be implanted using special drill guide instrumentation. Anchoring screws are locked into the stem of the femoral component, while self-cutting threads on the screw head engage the pre-drilled medial cortex. This novel fixation principle can also be applied to other joint prostheses, e.g. finger, shoulder, elbow and knee, as well as to dental and spinal implants.

45 Claims, 6 Drawing Sheets

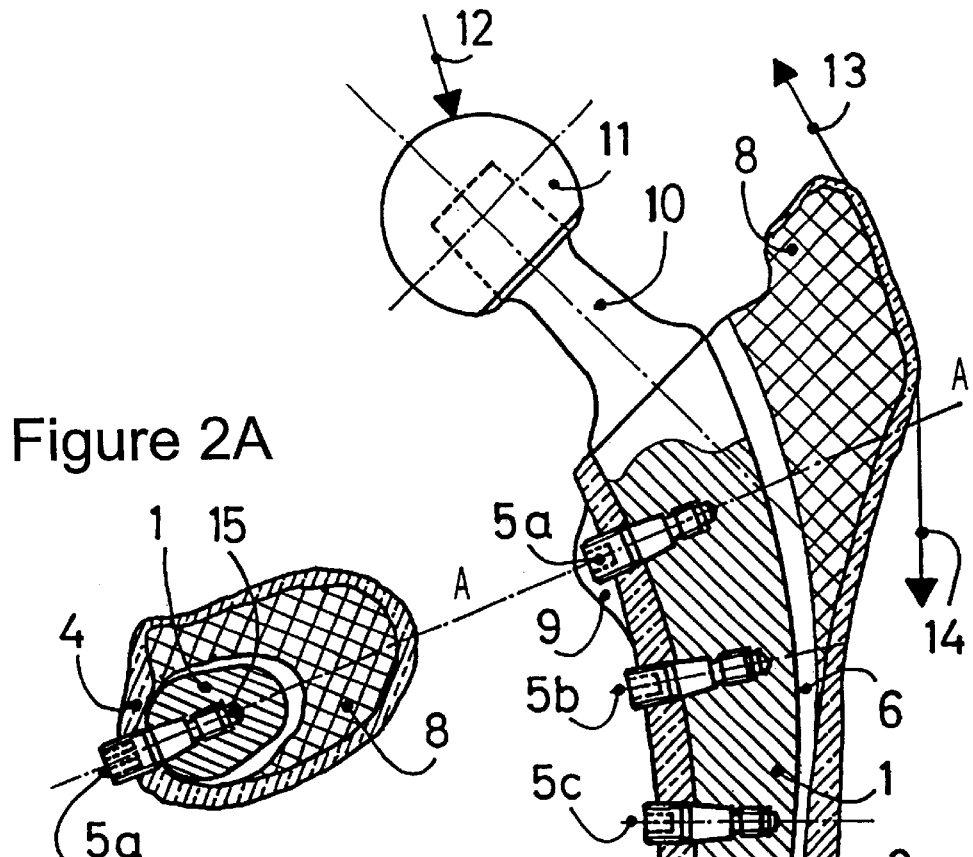
Figure 2A
Figure 2B
Figure 2
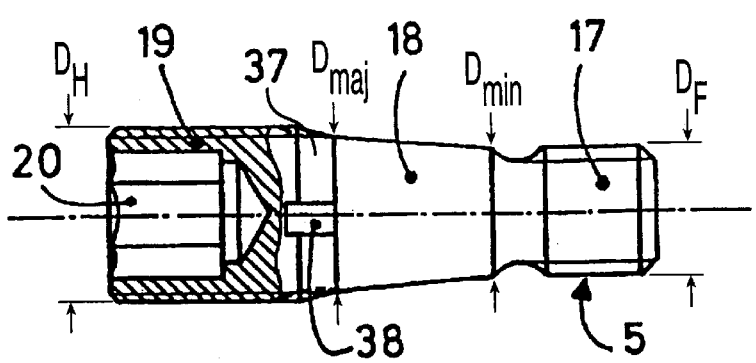
Figure 3

SCREW ANCHORED JOINT PROSTHESIS

TECHNICAL FIELD

The present invention generally relates to an improved joint prosthesis.

BACKGROUND OF THE INVENTION

In just over three decades since the inception of its widespread use, total hip replacement (THR) has changed the practice of orthopedic surgery. An entire new industry has been created to support THR and, more importantly, THR has improved quality of life of millions of patients to the extent unparalleled by any other single procedure in the history of surgery. All of this was originally made possible with the advent of cemented THR. Within the first decade following the pioneering work of Charnley, a broad base of trained surgeons, a highly motivated industry and compliant medical insurance policies have led to a world-wide acceptance of THR, evidenced by an exponential growth in the number of procedures being done, currently over 600,000 annually in the world.

This early period of unrestrained optimism was followed, however, by a wave of innovations after the longer-term results became available and the number of revisions (exchange or removal of one or both of the femoral and acetabular components of a THR) started to climb as well. Most of the blame for the increasing revision rate was placed on the bone cement, and efforts to eliminate it, by so-called cementless anchorage, dominated the next decade. But once again, the long term clinical outcomes forced a policy change—cementless THR designs did not match the standard set by the cemented, Charnley-type hip prosthesis design.

In spite of reasonably uniform medical training programs, and widely available and read professional literature, significant differences in attitudes controlling the practice of THR in different geographic regions persist until today and will probably continue to do so. There are countries where over 95% of THR procedures are cemented (e.g. Sweden), but also those where cementless have an edge (e.g. Germany, with about 2 out of 3 THR being cementless). Hybrid THR (i.e., in which one component is cemented and the other is not) has also gained a strong following, especially in the U.S., usually with the acetabular component being cementless and the femoral stem cemented, although the opposite approach has some supporters as well, and the latter is not without merit in view of some recently published clinical outcomes.

The Swedish Hip Registry (and the more recently implemented registries in Norway and in Finland) has been instrumental in weeding out approaches that perform poorly. However, only a limited number of the hip designs currently available worldwide are used in Sweden in numbers large enough to draw any conclusions. Many failures of innovation have also produced a very cautious surgical community, especially in Scandinavia. As the result of this practice of monitoring and control over selection of implants and surgical techniques, imposed by publishing the data from the Registry (including the performance of individual clinics), only one out of ten THR procedures currently done in Sweden is a revision. In comparison, less precise data suggests that one out of five THR procedures in the U.S. is a revision, and the number may be as much as one out of three or four in Germany.

Frequency of revision surgeries depends on many factors other than prosthesis design. However, it is indisputable that one of the primary factors is the still-superior performance of the cemented THR in comparison to cementless. In the Swedish Registry, the overall rate of revisions of cementless THRs is double that of cemented THRs using modem cementing techniques. The debate has come to be dominated by the use of a single outcome parameter of THR—one that the Swedish Registry is based on—the THR "survival rate." The survival rate of a THR design is defined as the percentage of such THRs which remain in the patient (i.e., which are not revised). Since the survival rate is approximately 95% at ten years for a good prosthesis and a good cement, properly used, it seems that there should be much less pressure for innovation than suggested by the variation of THR models present on the market and by the continuing efforts to improve cementless designs and cementing techniques. One of the reasons spurring new innovation is that both the surgeons and implant manufacturers need something new to gain recognition and market share, which is difficult to do in the non-differentiated field of cemented Charnleys.

Despite the 95% ten-year survival of cemented THRs, it is recognized that there are real problems to solve in the long run. Accordingly, the Swedish Registry has recently undertaken a project to estimate the performance of a smaller number of cases which have not been revised (and thus, until now, were not entering the Registry with an outcome). It is anticipated that the results will show that some 15% of patients have a failed THR at 10 years, but have not been revised for various reasons, such as the advanced age (and limited remaining life expectancy) of the patient. In younger patients revision rates are higher, and cementless THRs currently available seem not to have made any positive impact.

Thus, the limitations of conventional approaches to THR which need to be solved in the long run can be summarized as follows:

in properly-designed cemented stems, most of the failures are due to limited fatigue endurance of the bone cement (leading to so called aseptic loosening);

in cementless stems most of the failures are due to bone loss induced by movement at the stem-bone interface;

in acetabular components, difficulty of matching the implant to highly compliant cancellous bone, with or without cement, leads to formation of soft tissue at the interface which may progress to gross instability;

biological response to wear debris, produced at all interfaces at which relative movement occurs, by intent or accident, including the artificial joint itself, can lead to activation of bone resorption, so called osteolysis, which may progress to gross loosening of prosthetic components, or even to bone fractures.

The invention described herein successfully addresses the challenges of interfacing prosthetic components to bone, allowing the patients unrestricted use of the replaced joint in the immediate post-operative period, yet providing a stable anchorage to the bone of unlimited duration. The invention is disclosed in full detail on an example of the femoral component of a total hip prosthesis, but it is clear that the same principles can be applied to many other prosthesis, e.g. shoulder (humeral component), elbow (both components), knee (both components), finger (both components). It is also applicable to dental and spinal implants. In this disclosure those other applications are only sketched—one skilled in the art of designing and using such components could certainly, following the example of the total hip prosthesis, produce all necessary implants, instruments and insertion procedures.

The present invention removes a drawback of the screw-fixed femoral components for total hip prosthesis known in the prior art, as exemplified by U.S. Pat. No. 5,458,654 ("the '654 patent"), namely the necessity to drill access holes in the lateral cortex of the proximal (or upper) femur, and the concomitant need to make incisions in the soft tissue and muscle overlying the lateral cortex. It will of course be appreciated by those of skill in the art that any unnecessary trauma to soft tissue or bone is preferably to be avoided, due to the trauma to the patient's body, weakening of the femur due to removal of healthy bone matrix, and the chance for infection.

SUMMARY OF THE INVENTION

It is one object of the present invention to provide an orthopaedic implant system comprising an orthopaedic implant and at least one bone screw. The orthopaedic implant comprises an intraosseous portion, which intraosseous portion has a first side; a second side; and at least one screw hole. The screw hole has an entry opening at the first side and an internally-threaded portion. The bone screw has an externally-threaded, front end for engagement with the internally-threaded portion of the screw hole, and an externally-threaded head for engagement with the bone. When the front end of this screw is engaged with the internally-threaded portion of the screw hole, the screw is locked to the implant by the interaction of parts of the screw and implant other than the front end of the screw and the internally-threaded portion of the screw hole.

This orthopaedic implant system may be used with a bone having a near cortex, a far cortex, and an intraosseous region; in this case, the externally-threaded head of the bone screw engages with the near cortex of the bone, thereby coupling the orthopaedic implant to the bone in close apposition to (the interior surface of) the near cortex. The screw hole may be either a blind hole, or a through hole which extends to the second side of the intraosseous portion, in the latter case, the front end of the screw may engage with the far cortex of the bone. The bone screw may further be provided with a transition portion, located between the front end and the head, the transition portion provided with self-tapping flutes. The threads of the front end of the screw may have a pitch substantially the same as the threads of the head.

This orthopaedic implant system may include a guide which locks to the implant and has guide holes coaxial with the screw holes in the intraosseous portion when the guide is locked to the implant.

The screw hole may also have a conically tapered portion decreasing in diameter from the entry opening towards the second side. The conically-tapered intermediate portion of the screw preferably has a half-cone angle of about 1 to about 15 degrees, or more preferably of about 3 to about 8 degrees, and most preferably about 5 degrees. The corresponding bone screw will have a conically-tapered intermediate portion tapering from a major diameter near the head to a minor diameter near the front end, with a taper generally matching that of the screw hole.

In this system, it is preferable that the second thread diameter is greater than the major diameter of the intermediate portion and the first thread diameter is less than the major diameter of the intermediate portion. The engagement of the front end of the bone screw with the internally-threaded portion of the screw hole when the screw is inserted into the intraosseous portion draws the conically tapered portion of the screw into engagement with the conically tapered intermediate portion of the screw hole as the screw is advanced, thereby locking the screw and the orthopaedic implant.

It is yet another object of the present invention to provide an embodiment of the implant system which is a hip joint prosthesis. In this embodiment, the implant comprises a femoral component having an intramedullary stem. The intramedullary stem has a medial side, a lateral side, and at least one screw hole. This hip joint prosthesis is suitable for use with a femur having a medial cortex, a lateral cortex, and an intramedullary region, in which case the externally-threaded head of the bone screw engages with the medial cortex, thereby coupling the femoral component to the femur in close apposition to (the interior surface of) the medial cortex.

It is yet another object of the present invention to provide an improved method for implanting an orthopaedic implant in a bone having a near cortex and a far cortex, using screws rather than cement, the implant having an intraosseous portion to be implanted into the patient's bone. The improvement comprises: inserting the intraosseous portion into the bone of the patient; inserting a bone screw first through the near cortex and then into the implant such that the front end of the screw engages with the intraosseous portion of the implant and the head of the screw engages with the near cortex of the bone; and coupling the orthopaedic implant to the bone in close apposition to (the interior surface of) the near cortex.

This method can also include the steps of: providing an orthopaedic implant having an intraosseous portion having at least one screw-receiving hole; drilling a screw hole in the near cortex of the bone, with no corresponding coaxial hole in the second cortex of the bone, the hole being substantially aligned with the screw-receiving hole in the intraosseous portion; and wherein the step of inserting the bone screw includes inserting the screw through the screw hole in the near cortex and into the screw-receiving hole, such that rotation of the screw advances it in a direction from the near cortex of the patient's bone towards the far cortex. such that rotation of the screw advances it in a direction from the near cortex of the patient's bone towards the far cortex and the bone screw engages with the screw hole in the far cortex.

The method can further comprise the step of providing a bone screw having an externally-threaded front end and an externally-threaded head. In this case, when the anchorage screw is inserted into the screw hole in the near cortex and into the screw-receiving hole, the threads of the front end of the screw may engage with the threaded section of the screw-receiving hole before the threads of the head engage the near cortex. The method can further comprise the step of providing a bone screw having a conically-tapered intermediate portion which tapers from a minor diameter towards the front end to a major diameter towards the head, and a transition portion between the intermediate portion and the head, the transition portion being provided with self-cutting flutes. In this case, when the anchorage screw is inserted into the screw hole in the near cortex and into the screw-receiving hole, the threads of the front end of the screw may engage with the threaded section of the screw-receiving hole before the self-cutting flutes of the transition portion engage the near cortex.

The method can further comprise the steps of providing a guide which locks to the prosthesis and has guide holes coaxial with the screw holes in the intraosseous portion when the guide is locked to the prosthesis and using the guide holes in the guide to drill screw holes in the near cortex of the patient's bone.

It is yet another object of this invention to provide a method, which can advantageously be used for implanting a femoral component of a hip joint prosthesis in the intramedullary canal of the patient's femur, according to the principles summarized above.

It is yet another object of this invention to provide a femoral component for a cementless hip joint prosthesis, the femoral component comprising an intramedullary stem for insertion into the intramedullary region of a femur, wherein a single size of the intramedullary stem is suitable for use with a wide range of femur sizes. This femoral component can advantageously be used in a method permitting the provision of a femoral component having a stem of one size to fit a wide range of femur sizes.

BRIEF DESCRIPTION OF THE DRAWINGS

The features and advantages of the present invention will become more readily apparent from the following detailed description of the invention in which like elements are labeled similarly and in which:

FIG. 2 is a frontal plane section of the femoral component of a hip prosthesis according to present invention;

FIG. 2A is a transverse sectional view along line A—A of FIG. 2;

FIG. 2B is a transverse sectional view along line B—B of FIG. 2;

FIG. 3 is a partial side view and partial frontal plane section of the anchorage screw according to the present invention;

DETAILED DESCRIPTION OF THE PREFERRED EMBODIMENTS

The Prior Art

As discussed in detail above, there is an extensive art relating to cemented and cementless hip prosthesis, such art having problems identified therewith, including failures due to limited fatigue endurance of the bone cement; bone loss induced by movement at the stem-bone interface; formation of soft tissue at the interface which may progress to gross instability; and osteolysis, which may progress to gross loosening of prosthetic components, or even to bone fractures. Although the design disclosed in the '654 patent resolves many of these problems, it still presents room for some improvement from the surgical perspective.

Figure 1:
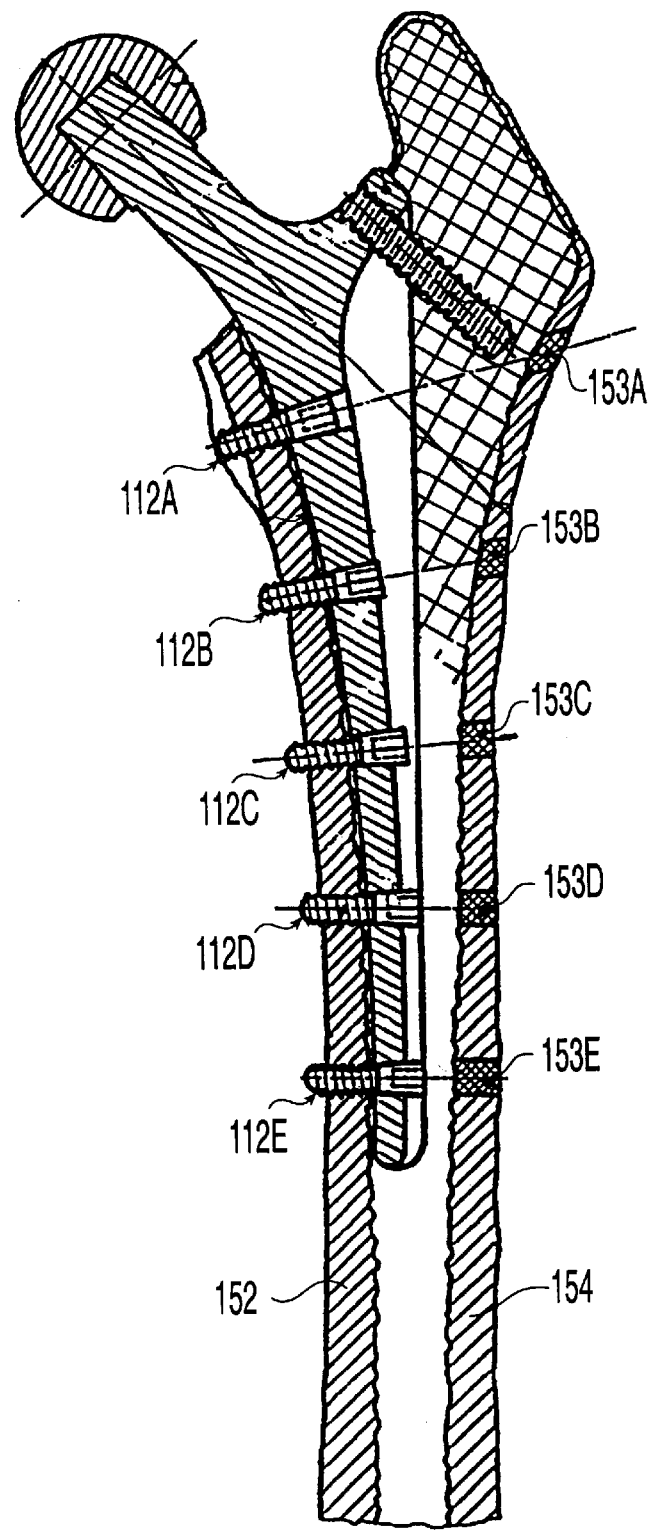
FIG. 1 is a frontal plane section of the cementless femoral component of a hip prosthesis according to the prior art.

A cementless, screw-fixated femoral component as known in the art, and such as disclosed in the '654 patent, is shown in FIG. 1. The screws 112A to 112E securely attach the femoral component to the medial cortex 152, thus overcoming some of the problems with cemented femoral components. However, this design requires some trauma to parts of the patient's body which is not required for the long-term component fixation. For example, the design of the screws 112 requires that they first be inserted through the stem 101 of femoral component, and second be inserted into, and engage with, the medial cortex 152. Because of this design, the surgeon must drill clearance holes 153A to 153E in the lateral cortex 154. These clearance holes must be of relatively large diameter, as they must permit passage of the entire screw, including the head. Of course, in order to make these clearance holes, the surgeon must first cut through the soft tissue and muscles to access the lateral cortex. It will be appreciated that the tissue incisions and clearance holes on the lateral aspect of the femur are not actually required for the ongoing fixation of the femoral component to the bone, but are rather simply required to permit the implantation process based on the prior art prosthesis design.

Anchorage of the Femoral Component of a Total Hip Prosthesis According to Present Invention FIG. 2 is a cross section of the proximal (or upper) femur with a femoral component of the total hip prosthesis of the present invention anchored in place. The section is taken in the plane of the implant which corresponds to the plane of the resected femoral neck (which is usually rotated into antiversion, i.e. pointing the head forward, by some 10 to 15 degrees). As in a conventional prosthesis, the stem 1 of the prosthesis is placed within the medullary cavity 2 of the femur 3. In contrast to a conventional cemented prosthesis however, the stem is anchored by a plurality of screws, 5a through 5e, to the medial cortex 4 alone, with no engagement of the lateral cortex 7. Using this fixation system, the femoral component is rigidly coupled to the femur in close apposition to the interior surface of the medial cortex. The cortices of the bone under consideration may generally be given context-specific denominations, such as the "first" and "second" cortices, or the "near" and "far" cortices. In the latter case, it is to be understood that the "near" cortex is the cortex which is closer to, or is facing, the surgeon considering the bone in a particular situation. Conversely, it is to be understood that the "far" cortex is the cortex which is further from, or is facing away from, the surgeon.

Preferably, there should be a gap 6, i.e. no contact, between the stem 1 and the lateral cortex 7 of the femur 3. This gap will preferably extend along the entire length of the stem. In other words, at no point along its length does the stem fill the medullary canal. Because the stem only partially fills the medullary canal, it allows for the bone to continue to experience most of its normal loading stresses, and does not subject the bone to the hoop stresses which result from know cementless or press-fit designs. Furthermore, the partial-filling aspect of the stem of this invention allows for a single size of prosthesis stem to fit a very wide range of femur bone sizes. In contrast, known systems must provide as many as a dozen stem sizes in order to fit a variety of femur sizes. The aim of such a placement and anchorage is to avoid the relative movement (and hence debris production and bone resorption) between the stem.and the bone. Soft cancellous bone 8 in the proximal part of the femur may eventually grow to fill the gap 6, but the stability of the prosthesis does not require stable, direct bony contact in this area. The most proximal screw 5a is located approximately at the level of the lesser trochanter 9. The femoral component neck 10 is conventional, and so is the head 11. Preferably the head is modular, and made of ceramic or metal.

Under weight-bearing conditions, joint force 12 is directed along the medial fixation and the loads imparted to the anchorage screws 5a–5e are mostly in shear. The muscles of the leg attached to the greater trochanter generate a force 13 pulling up towards the pelvis, as well as a force 14 down towards the knee. In conventional, medullary canal-filling stems, anchored by press fit, the resulting deformations of the femur lead to unavoidable movements between the stem and the bone, in one or the other aspect of the interface. These shear, or "rubbing" movements are primarily to blame not only for the ultimate consequences of component loosening, but also for thigh pain, which is a very frequent clinical complication of cementless fixation. In some patients this condition can become chronic.

FIG. 2A shows a transverse cross section at the level of the most proximal screw. The anchorage screw 5a is seen to be inserted into the screw receiving hole 15 of the stem 1. The screw engages both the stem 1 and the medial cortex 4. It is important for the proper function of the anchorage screw that it fill the medial portion of the screw hole as well as being rigidly engaged with, or locked within, the stem 1, so that it can transmit bending loads as well as shear and axial loads.

As seen in FIG. 2, in the illustrated situation the distal (or lower) part of the stem 1 is too narrow relative to the screw length, such that the screw is not contained completely within the stem. Accordingly, the screw hole for that screw is not a "blind" hole, but is rather a through hole extending through the diameter of the stem to the lateral side. The opening of the screw hole on the lateral side of the stem, the lateral hole exit, undesirably creates a stress riser or stress concentration. Thus, in order to reduce the stress concentration around the lateral hole exit, a recess 16 is cut into the lateral aspect of the stem. This recess can be seen in transverse section in FIG. 2B.

Although the most proximal screw 5a is shown to be a short screw in a blind hole, in another embodiment this hole and screw may be modified for different performance characteristics. In that embodiment, the hole can be made into a through hole, going all the way through the prosthesis from the medial side to the lateral side, and the screw 5a would be provided with a sufficient length to engage the lateral, or far, cortex bone on the other side of the medullary canal, including the cancellous region 8 and preferably also the lateral cortical bone 7. The screw 5a would then be supported in the femur bone at two locations, thus serving to carry torsional loads which might otherwise be concentrated at a single location.

The design of the anchorage screw is seen in more detail in FIG. 3. This bone screw has a cylindrical small-diameter front end portion 17, provided with machine-type threads on its exterior surface; a conically-tapered intermediate portion 18; and a cylindrical head, or bone-engaging portion 19, with a recess 20 for the insertion tool (such as a screwdriver). The head 19 is externally threaded, preferably with threads of substantially the same pitch as that of the threads of portion 17. There may be a transition portion 37 between the intermediate portion and the head. This transition portion is preferably supplied with self-tapping, or cutting, flutes 38. When the screw is rotated into place, these flutes initiate the cutting of the threads in the medial cortex which engage with the threads of the head.

The head has a thread diameter (the diameter as measured to the tops of the screw threads) of $D_H$, the intermediate portion has a major diameter $D_{maj}$ at its large-diameter end, and a minor diameter $D_{min}$ at its small-diameter end, and the front end has a thread diameter of $D_F$. The various diameters can be varied for the particular application but, for proper rigid locking of the femoral component to the femur, preferably will obey the relationship $D_F \leq D_{maj} \leq D_H$. In other words, the thread diameter of the front end should be smaller than the major diameter of the tapered intermediate portion, which in turn should be less than the thread diameter of the head. With a screw and corresponding hole designed according to that relationship, both the threaded portions and the tapered portion of the screw will properly perform their respective load-carrying functions.

The taper angle of the intermediate portion or cone 18 need not be as shallow as that typically required for friction locking under the "Morse taper" design, because its locking within the screw-receiving hole 15 in the stem is guaranteed by the pull of the threaded portion 17. A preferable range for the half-cone angle (the angle on each side of the centerline, i.e. one half of the total cone angle) is about 1 to about 15 degrees; for this application (hip prosthesis) the angle is most preferably about 5 degrees. With this angle, the cone can be safely locked within the receiving hole and thus strengthen (support) the stem along the medial side from within the screw holes. This is important for the overall stem strength—left empty, or improperly filled by the screws, screw holes could lead to stem fatigue failure.

Although the rigid locking of the screws in the holes could be achieved purely by mating threads on the screw and implant, such threaded relation is difficult to machine precisely enough to avoid micro-movement after implantation. Such motion is undesirable, as it may lead to fretting, corrosion, and other wear-related problems. The matching taper design of the present invention provides an intimate, rigid locking of the screw to the implant without these micro-movement problems. However, the locking of the screws in the holes need not be by the matching tapers of the embodiment shown in the figures. What is important is that the screw locks to the implant providing rigid fixation in response to axial, shear, and torsional loads. For example, in another embodiment, the implant could be made in part or in full from a soft material (such as soft metal, composite, or plastic) with no pre-formed screw holes, or with screw holes which are only partially formed. In this embodiment, the screw may tap its own threads in the stem, and thus achieve rigid locking of the screw to the component without the use of the tapers. In yet another embodiment, the screw hole could still have a threaded portion, and the screw could have a tapered portion, but the screw hole would not have a tapered portion corresponding to the taper on the screw. Rather, the part of the screw hole accepting the tapered portion of the screw is provided with an insert made of soft material, such that as the screw is advanced into the hole, the taper of the screw compresses the insert, and in that way achieves rigid locking of the screw to the component.

The hip joint is approached by a conventional incision and anterior lateral approach. Once the hip joint is exposed, it is dislocated to separate the femur from the pelvis and to allow access to the femoral neck. The femur is then cut at the base of the neck to separate the head and neck from the balance of the femur. The exposed cancellous bone in the proximal femur is drilled to expose the medullary canal. Then a broach, or file, is applied to the medullary canal to widen it sufficiently to accept the stem of the femoral component.

Figure 4:
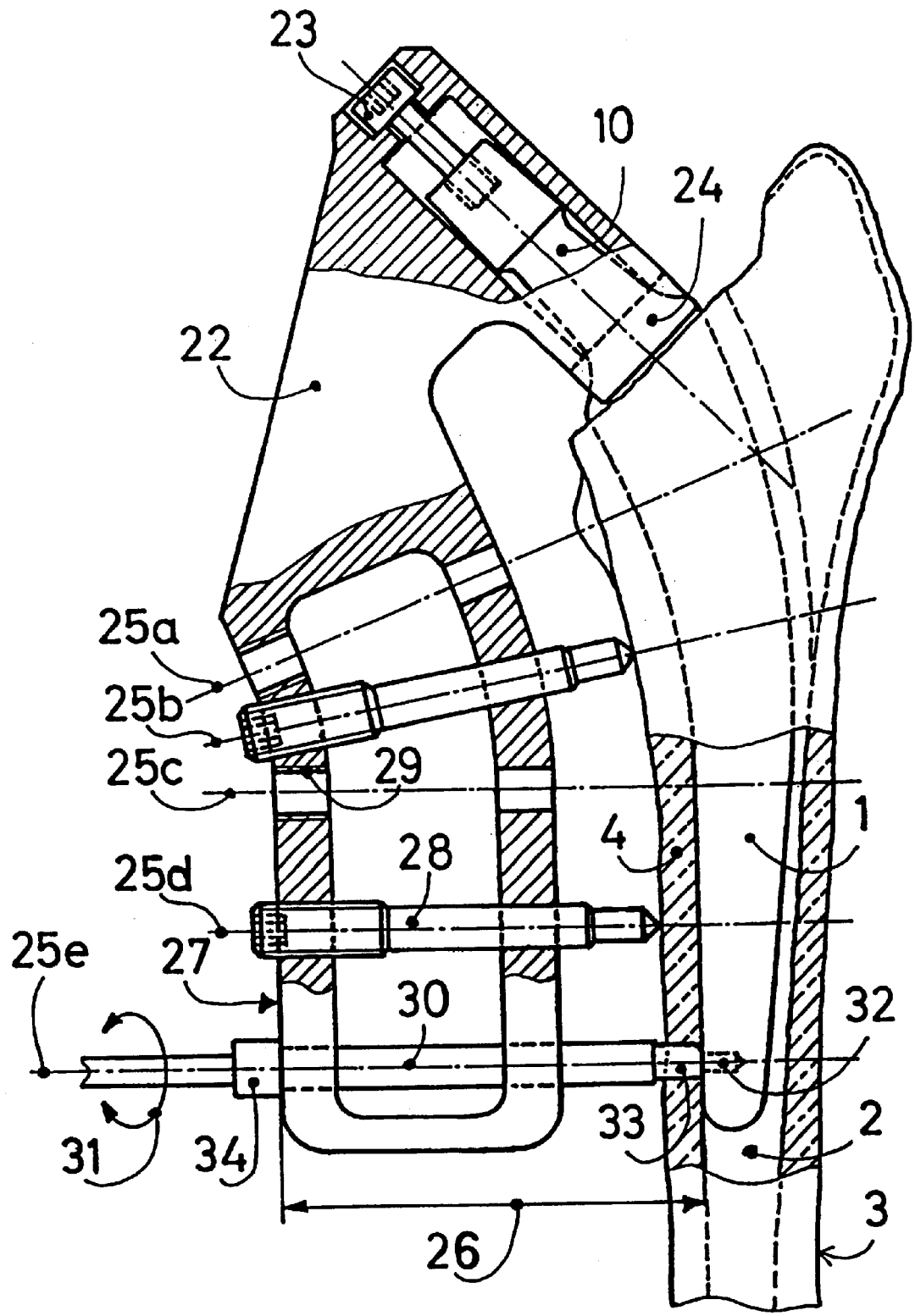
FIG. 4 is a partial side view and partial frontal plane section view of a femoral component according to FIG. 2 also showing an insertion/drilling guide and associated instrumentation.

Insertion of the prosthesis and its anchoring to the proximal femur is preferably accomplished with the aid of special instruments, as shown in FIG. 4. In sharp contrast to the approach required by known screw-fixated femoral components such as that disclosed in the '654 patent (and illustrated in FIG. 1), the implantation uses a medial approach. The femur is externally rotated to an extreme position, allowing the surgeon access to the medial aspect of the bone. The muscles are separated to allow placement of the implant and guide assembly. As described in more detail below, the screws are inserted from the medial direction into the bone towards the lateral direction, between the major muscle insertions.

The guide 22, which facilitates insertion and drilling, is securely locked to the stem over the neck 10 by means of a screw 23, and the rotational position (around the neck axis) between the prosthesis and the guide is fixed in the shoulder region 24 of prosthesis. Guide holes 25a through 25e in the body of the guide are provided to be coaxial with the orientation of the screw-receiving holes in the stem 1 when the guide and femoral component are thus locked together.

The drill guide 22 is preferably shaped such that the distance 26 between the medial stem surface and the medial surface 27 of the guide is equal for all screw positions. Once the stem 1 is placed into the medullary canal 2, the prosthesis can be temporarily held in the proper position by inserting one or two partially threaded positioning bolts 28 into the drill guide and screwing them into the guide until their tips push against the medial, or near, cortex. This results in close apposition of the stem 1 against the interior surface of the medial cortex 4. Medial portion(s) 29 of some, or all, of the drill holes may be threaded to receive the threaded positioning bolts 28.

Once the surgeon judges the position of the stem within the femur as correct (including the desired angle of antiversion), an anchorage screw hole is drilled in the medial cortex 4 by means of a special drill 30. In order to minimize damage to soft tissues, which may, but need not be, fully retracted from the bone, an oscillating drilling machine can be employed to drive the drill with a back-and-forth motion, as indicated by arrow 31. The front portion 32 of the drill 30 has a diameter which is slightly smaller than the receiving hole 15 in the stem 1. Thus the portion 32 of the drill and the hole 15 form a centering system which automatically leads the final drilling of the cortex by the cutting portion 33 of the drill 30 to be properly coaxially aligned with the center of the receiving hole. The diameter of the hole produced by the drill portion 33 should be equal or slightly smaller than the core (thread base) diameter of the threaded screw head 19 of the anchoring screw 5, as seen in FIG. 3. Drill 30 may be provided with a shoulder 34 limiting the penetration of the drill to the exact pre-determined depth.

After the first anchorage screw is inserted, preferably in an intermediate position along the length of the stem, the other anchorage screws are inserted one at a time through the holes in the guide which do not have positioning bolts in them. Then the positioning bolts 28 are removed and anchorage screws are inserted at those positions as well. After the femoral component has thus been firmly engaged with the femur, the balance of the implantation procedure follows the standard procedures as for known hip prosthesis.

Screw Hole Geometry

Figure 5:
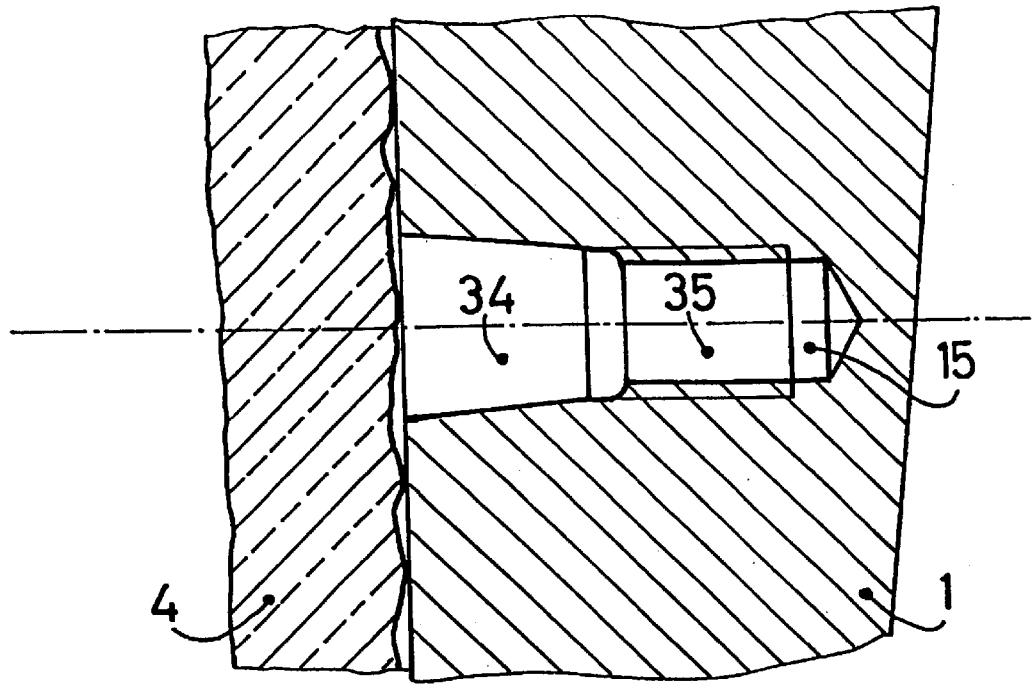
FIG. 5 is a frontal plane section view of a detail of the screw-receiving hole in the prosthesis stem of the prosthesis shown in FIG. 2.

The shape of the screw-receiving holes 15 in the stem 1 is shown in detail in FIG. 5, in which stem 1 is shown in close apposition to the interior surface of medial cortex 4. It will be seen that some of the screw holes (specifically, those associated with screws 5a–5c) are "blind" holes which do not extend all the way through the stem from the lateral side to the medial side, while others (specifically, those associated with screws 5d and 5e) are "through" holes which do extend from one side of the stem to the other. The end portion, 35, of the hole 15, is an internally-threaded portion which receives the front end, or stem-engaging, portion 17 of the screw 5 (as seen in FIG. 3). The screw hole has an entry opening at the medial surface of the stem and a conically tapered portion 34 having a conical tapered shape which corresponds to the conically tapered intermediate portion 18 of the anchoring screw 5 (as also seen in FIG. 3). The diameter of the intermediate portion decreases from the end of the intermediate portion close to the entry opening towards the medial side of the stem.

Figure 6:
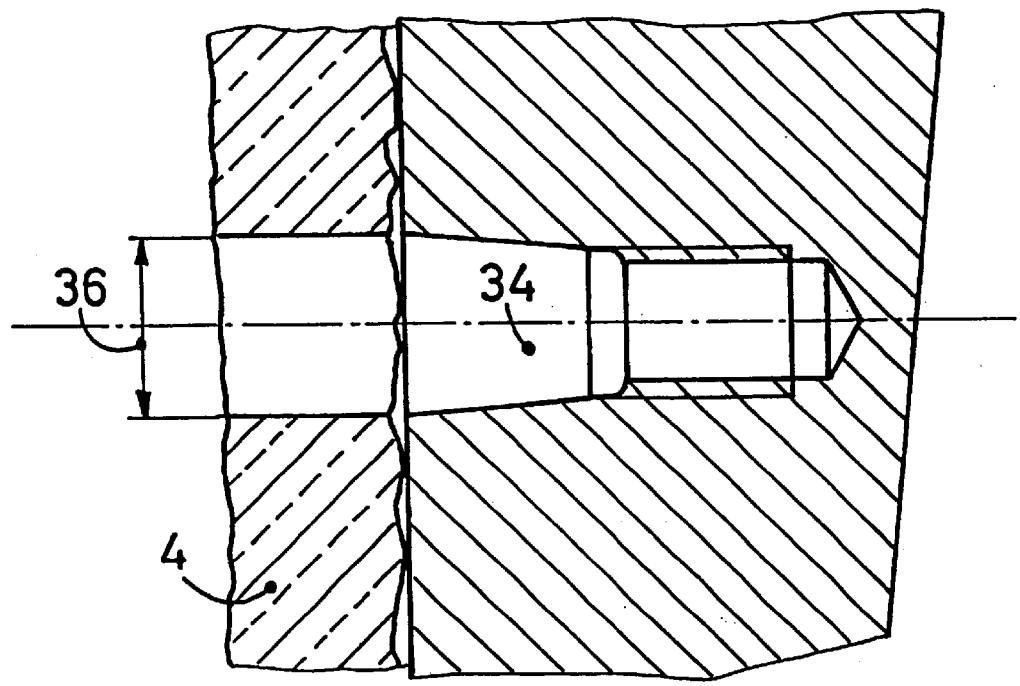
FIG. 6 is a frontal plane section view of a detail of the screw receiving hole of FIG. 5, also illustrating the corresponding hole drilled in the bone.

FIG. 6 shows the situation after the corresponding hole is drilled in the medial cortex of the femur (as illustrated in FIG. 4). The diameter 36 of the hole in the medial cortex 4 is preferably equal to, or slightly smaller than, the core (thread base) diameter of the threaded bone-engaging portion 19 of the screw head. The entry diameter 36 is preferably about the same as the entry diameter of the conical portion 34 of the receiving hole. Once the hole is drilled in the medial cortex, the anchorage screw can be inserted.

Preferably, the screw and hole are dimensioned such that the front end 17 of the screw 5 engages the threaded portion 35 in the stem 1 before the transition portion 37, supplied with the cutting flutes 38, starts to cut the threads in the bone. In this way there should be no pre-stresses within the system, as could occur if the threads in the bone are cut before the screw-stem engagement. The screw is firmly inserted so as to pull the conical portion 18 of the screw into receiving portion 34 of the screw hole.

Figure 7:
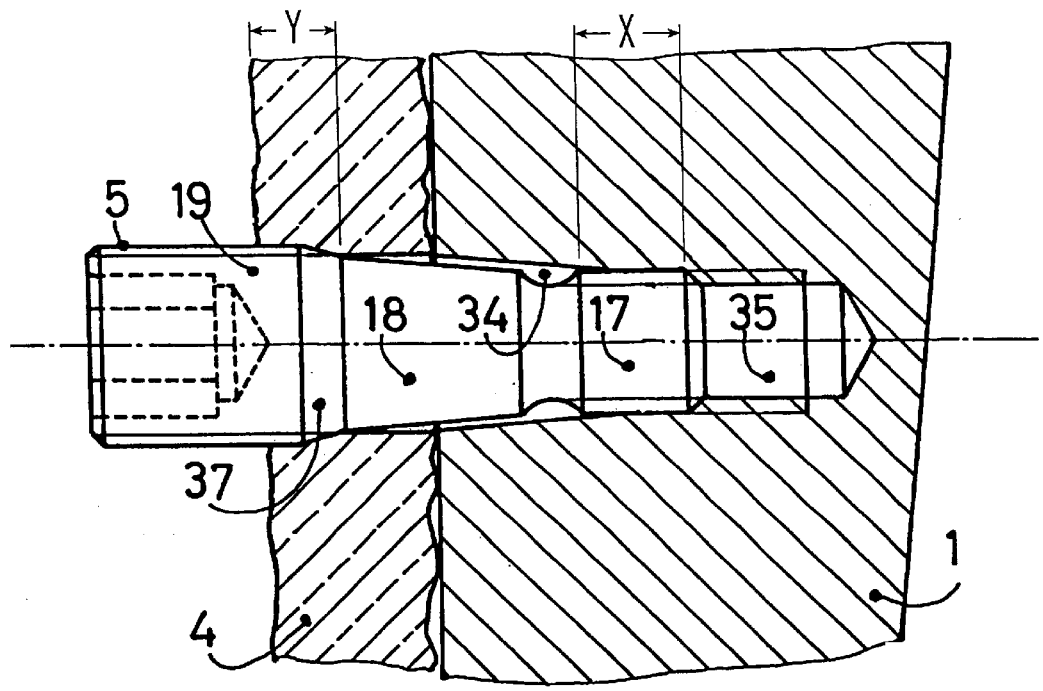
FIG. 7 is a partial side view and partial frontal plane section view showing the bone-tapping anchorage screw of FIG. 3 partially inserted into the bone and femoral component.
Figure 8:
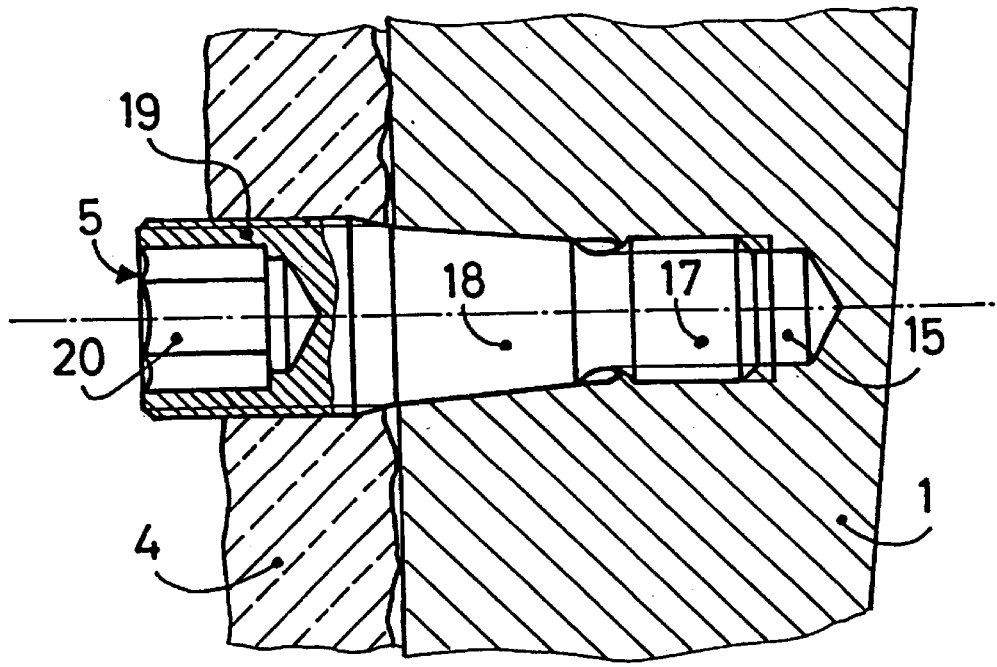
FIG. 8 is a partial side view and partial frontal plane section view showing the bone-tapping anchorage screw of FIG. 3 fully inserted into the bone and femoral component.

FIG. 7 shows the anchorage screw at an intermediate position of insertion into the stem and bone. The threads on the stem-engaging portion 17 have engaged with the threaded portion over a depth "X", whereas the threads on the bone-engaging portion 19 have cut into and engaged with the bone over a lesser depth "Y." In FIG. 8, the anchorage screw 5 is shown fully inserted into the hole 15 in the stem 1. The threads on the front end 17 fix the screw to the femoral component, while the threads on the bone-engaging portion 19 fix the screw to the medial cortex 4. In this way, the screw mechanically fixes the stem 1 to the medial cortex 4. It is evident from FIG. 8 that even in the "fully" inserted position, some part of the screw head 19 may still extend beyond the surface of the medial cortex.

As mentioned earlier, it is important for the screw to be rigidly locked to the stem, so that any bending moments can be resisted without the tilting of the screw within its screw hole. Use of conventional screws would lead to early loosening within bone caused by the tilting movements of such screws relative to the stem.

Applications of the Invention to Other Prosthesis and Implants

The main motivation for the current invention was to solve the problem of femoral component loosening in total hip replacements performed in younger patients. However, it will be appreciated by those of ordinary skill in the art that the principles of anchorage described above can be readily adopted to other implants, such as intramedullary nails, finger joint prosthesis, shoulder prosthesis, dental implants, and spinal implants. Indeed, the present invention has application in any orthopaedic situation in which there are two cortical bone areas (generally referred to as a first and second cortex, or, depending on the reference frame, a near and far cortex) on either side of an intraosseous bone area. The present invention can then be used to use a screw, inserted through the selected cortex of the bone, to secure the intraosseous portion of the orthopaedic implant to the bone in close apposition to the interior surface of that selected cortex, without the need for drilling the other cortex.

For example, an intramedullary nail may be interlocked to the broken bone segments using the method of fixation of the present invention. The anchorage screws for this embodiment may be made either unicortical or bicortical; if bicortical, the front of the screw should also be self tapping. The method of implanting this embodiment of the invention would involve the drilling of a hole in the near cortex, and also a coaxial hole in the far cortex, unlike the method illustrated in the figures herein.

Figure 9:
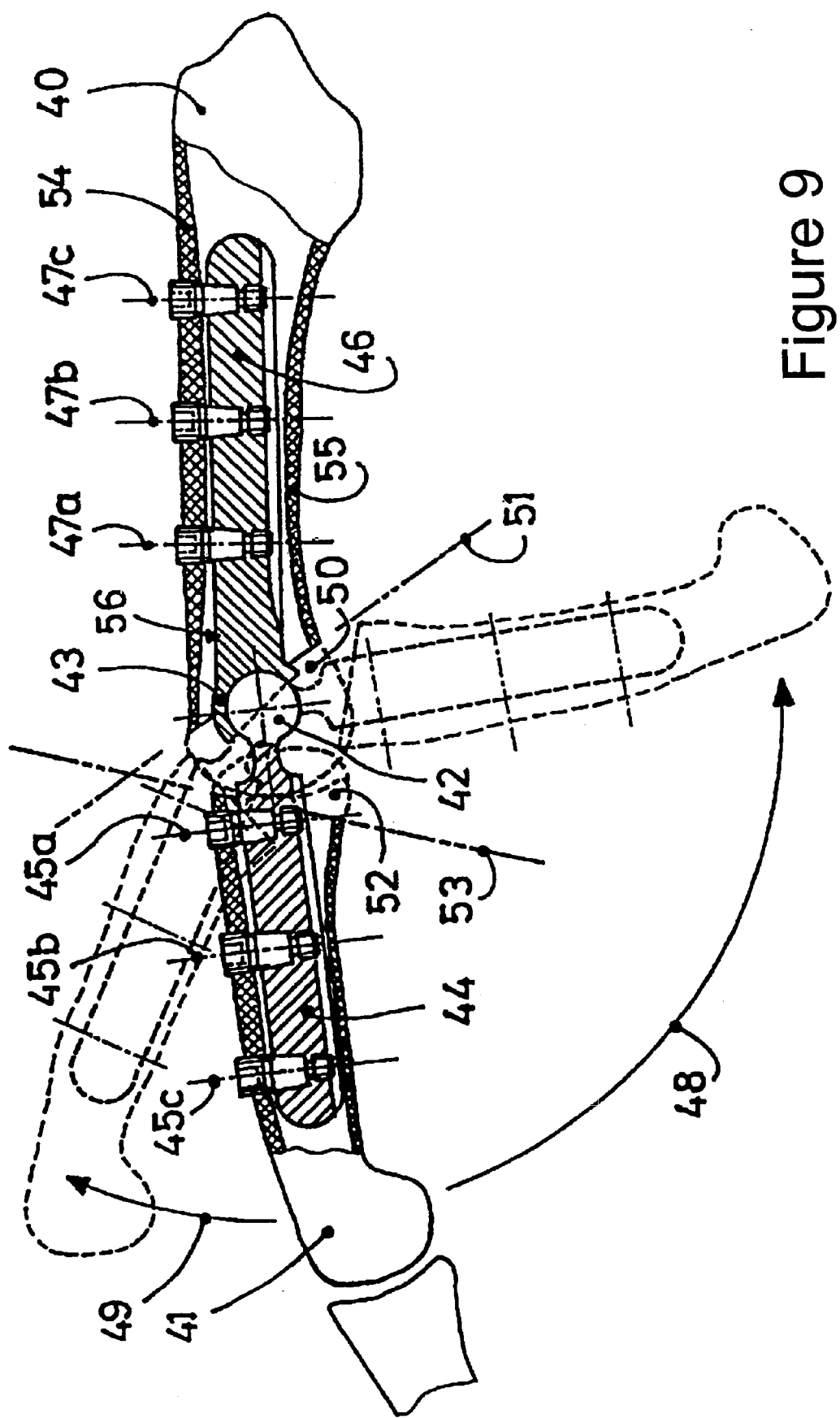
FIG. 9 is a partial side view and partial frontal plane section view of a finger joint prosthesis embodiment of the present invention.

FIG. 9 shows another embodiment of the present invention, where a natural joint between a metacarpal (palm) bone 40 and the first bone 41 of the corresponding finger is shown replaced by a total prosthesis 56 of the ball-and-socket type. The head 50 on the metacarpal bone of the normal joint is shown replaced by the socket 43 of the artificial joint, while the base (concave) side of the normal joint 52 is shown replaced by the ball 42 of the artificial joint. This reversal allows for a greater range of movement with a more convenient resection of the head 50 at the plane 51, and the base 52 at the plane 53. More than 90 degrees of flexion 48 is allowed without impingement of prosthetic components or bones, as well as over 30 degrees of extension 49—this is comparable to the natural range of this joint. The ball 42 of the prosthetic joint is carried on the distal stem 44 which is fixed by the method of the invention to finger bone 41 by screws 45a through 45c. The socket 43 of the joint is carried by the proximal stem 46 of the prosthesis fixed to the metacarpal bone 40, also according to the present invention, by screws 47a through 47c. Fixation to the dorsal cortices 54, as illustrated, is preferred because of the simpler surgical approach, but fixation to palmar cortices 55 is also possible.

Regardless of the specific orthopaedic application of the present invention, the use of screws for primary fixation does not preclude use of porous coatings, e.g. titanium plasma, hydroxyapatite, etc., for additional stabilization by bone ingrowth. If used, those coatings should preferably be applied only at the areas of the stem where the bone to stem movement is inhibited by the screws. For example, in the total hip prosthesis, preferably only the medial aspect of the stem is coated. This coating method is used to prevent the consequences of so-called "stress shielding" which can lead to massive long term loss of bone stock. Fixation to the medial cortex alone causes much less distortion in the normal stress pattern than fixation to both cortices. Also, the potential for re-vascularization of the bone is much higher if some parts of the medullary cavity are left intact, or at least not fully filled by the implant.

While the forgoing description and drawings represent the preferred embodiments of the present invention, it will be obvious to those of ordinary skill in the art that various changes and modifications may be made therein without departing from the true spirit and scope of the present invention.

What is claimed is:

1. An orthopaedic implant system for implantation in a patient's bone, the system comprising:
   an orthopaedic implant comprising an intraosseous portion, the intraosseous portion having:
      a first side
      a second side; and
      at least one screw hole, the screw hole having an internally-threaded portion;
   at least one bone screw having:
      an externally-threaded front end for engagement with the internally-threaded portion of the screw hole; and
      an externally-threaded head for engagement with the bone.

2. An orthopaedic implant system according to claim 1 wherein full engagement of the externally-threaded front end of the screw with the internally-threaded portion of the screw hole results in locking of the screw to the implant.

3. An orthopaedic implant system according to claim 2, wherein:
   the bone screw further comprises an intermediate screw portion between the front end and the head;
   the screw hole further comprises an intermediate hole portion; and wherein further the interaction of a part of the screw including the intermediate screw portion but excluding the front end, and a part of the implant including the intermediate hole portion but excluding the internally-threaded portion of the screw hole, contribute to the locking of the screw to the implant.

4. An orthopaedic implant system according to claim 1 wherein the system is for use with a bone having a near cortex, a far cortex, and an intraosseous region, and wherein further the externally-threaded screw head is configured to engage with the near cortex of the bone, so as to couple the orthopaedic implant to the bone in close apposition to the interior surface of the near cortex.

5. An orthopaedic implant system according to claim 4 wherein the screw hole is a through hole which extends from the first side to the second side of the intraosseous portion of the implant, and wherein further the screw is of sufficient length to enable the front end of the screw to engage with the far cortex of the bone.

6. An orthopaedic implant system according to claim 1 wherein the bone screw further has a transition portion, located between the front end and the head, the transition portion provided with self-tapping flutes.

7. An orthopaedic implant system according to claim 1 wherein the threads of the front end of the screw have a pitch generally the same as the threads of the screw head.

8. An orthopaedic implant system according to claim 1 further comprising a guide which locks to the implant, the guide comprising at least one guide hole and a locking portion, the implant further comprising an extraosseous portion, and wherein the guide hole is generally coaxial with the screw hole in the intraosseous portion of the implant when the guide is locked to the implant, the locking being accomplished, at least in part, by a screw engaging the locking portion of the guide and the extraosseous portion of the implant.

9. An orthopaedic implant system for implantation in a patient's bone, the system comprising:
   an orthopaedic implant comprising an intraosseous portion, the intraosseous portion having:
      a first side
      a second side; and
      at least one screw hole, the screw hole having:
         an entry opening at the first side,
         a conically-tapered intermediate hole portion decreasing in diameter from the entry opening towards the second side, and
         an internally-threaded portion located between the intermediate hole portion and the second side;
   at least one bone screw having:
      an externally-threaded front end for engagement with the internally-threaded portion of the screw hole, the front end having a first thread diameter;
      an externally-threaded head for engagement with the bone, the head having a second thread diameter; and
      a conically-tapered intermediate screw portion between the front end and the head, the intermediate screw portion tapering from a major diameter near the head to a minor diameter near the front end.

10. An orthopaedic implant system according to claim 9 wherein the second thread diameter is greater than the major diameter of the intermediate screw portion and the first thread diameter is less than the major diameter of the intermediate screw portion.

11. An orthopaedic implant system according to claim 9 wherein the front end of the bone screw engages with the internally-threaded portion of the screw hole when the screw is inserted into the intraosseous portion, this engagement drawing the intermediate screw portion into engagement with the intermediate hole portion as the screw is advanced, thereby locking the screw and the orthopaedic implant.

12. An orthopaedic implant system according to claim 11 wherein the system is for use with a bone having a near cortex, a far cortex, and an intraosseous region, and wherein further the externally-threaded screw head engages with the near cortex of the bone, thereby coupling the orthopaedic implant to the bone in close apposition to the interior surface of the near cortex.

13. An orthopaedic implant system according to claim 9 wherein the screw hole is a blind hole which does not extend to the second side of the intraosseous portion.

14. An orthopaedic implant system according to claim 9 wherein the screw hole is a through hole which extends to the second side of the intraosseous portion.

15. An orthopaedic implant according to claim 14 wherein further the front end of the screw engages with the far cortex of the bone.

16. An orthopaedic implant system according to claim 9 wherein the intermediate screw portion has a half-cone angle of about 1 to about 15 degrees.

17. An orthopaedic implant system according to claim 9 wherein the intermediate screw portion has a half-cone angle of about 3 to about 8 degrees.

18. An orthopaedic implant system according to claim 9 wherein the bone screw further has a transition portion, located between the intermediate screw portion and the screw head, the transition portion provided with self-tapping flutes.

19. An orthopaedic implant system according to claim 9 wherein the threads of the front end of the screw have a pitch generally the same as the threads of the screw head.

20. An orthopaedic implant system according to claim 9 further comprising a guide which locks to the implant, the guide comprising at least one guide hole and a locking portion, the implant further comprising an extraosseous portion, and wherein the guide hole is generally coaxial with the screw hole in the intraosseous portion of the implant when the guide is locked to the implant, the locking being accomplished, at least in part, by a screw engaging the locking portion of the guide and the extraosseous portion of the implant.

21. A hip joint prosthesis comprising:
a femoral component having an intramedullary stem, the stem having:
a medial side;
a lateral side; and
at least one screw hole, the screw hole having an internally-threaded portion;
at least one bone screw having:
an externally-threaded front end for engagement with the internally-threaded portion of the screw hole, the front end having a first thread diameter; and
an externally-threaded head for engagement with the medial cortex of the femur, the head having a second thread diameter.

22. A hip joint prosthesis according to claim 21 wherein: the screw hole further comprises:
an entry opening at the medial side;
a conically-tapered intermediate hole portion decreasing in diameter from the entry opening towards the lateral side; and wherein
the internally-threaded portion of the screw hole is located between the intermediate hole portion and the lateral side, and wherein further
the screw further comprises a conically-tapered intermediate screw portion between the head and the front end, the intermediate screw portion tapering from a major diameter near the head to a minor diameter near the front end.

23. A hip joint prosthesis according to claim 22 wherein the second thread diameter is greater than the major diameter of the intermediate screw portion and the first thread diameter is less than the major diameter of the intermediate screw portion.

24. A hip joint prosthesis according to claim 22 wherein the front end of the screw engages with the internally-threaded portion of the screw hole when the screw is inserted into the stem, the engagement drawing the intermediate screw portion into engagement with the intermediate hole portion as the screw is advanced, thereby locking the screw and the femoral component.

25. A hip joint prosthesis according to claim 24 wherein the prosthesis is for use with a femur having a medial cortex, a lateral cortex, and an intramedullary region, and wherein further the externally-threaded head of the bone screw engages with the medial cortex, thereby coupling the femoral component to the femur in close apposition to the interior surface of the medial cortex.

26. A hip joint prosthesis according to claim 22 wherein the screw hole is a blind hole which does not extend to the lateral side of the stem.

27. A hip joint prosthesis according to claim 22 wherein the screw hole is a through hole which extends to the lateral side of the stem.

28. A hip joint prosthesis according to claim 22 wherein the intermediate screw portion has a half-cone angle of about 1 to about 15 degrees.

29. A hip joint prosthesis according to claim 22 wherein the intermediate screw portion has a half-cone angle of about 3 to about 8 degrees.

30. A hip joint prosthesis according to claim 22 wherein the bone screw further has a transition portion, located between the intermediate screw portion and the screw head, the transition portion provided with self-tapping flutes.

31. A hip joint prosthesis according to claim 22 wherein the threads of the front end of the screw have a pitch generally the same as the threads of the screw head.

32. A hip joint prosthesis according to claim 22 further comprising a guide which locks to the femoral component, the guide comprising at least one guide hole and a locking portion, the femoral component further comprising a neck, and wherein the guide hole is generally coaxial with the screw hole in the stem when the guide is locked to the femoral component, the locking being accomplished, at least in part, by a screw engaging the locking portion of the guide and the neck of the femoral component.

33. An improved method for implanting an orthopaedic implant, using screws rather than cement, in a bone having a near cortex, a far cortex, and an intraosseous region, the implant having an intraosseous portion, the improvement comprising:
inserting the intraosseous portion of the implant into the intraosseous region of the bone;

inserting a bone screw first through the near cortex and then into the implant;

engaging the front end of the screw with the intraosseous portion of the implant; and engaging the head of the screw with the near cortex of the bone; thereby coupling the orthopaedic implant to the bone in close apposition to the interior surface of the near cortex.

34. The method of claim 33 further comprising:

providing an orthopaedic implant having an intraosseous portion having at least one screw-receiving hole;

drilling a screw hole in the near cortex of the bone; and drilling a screw hole in the far cortex of the bone, generally coaxial with the screw hole in the near cortex of the bone;

wherein the step of inserting the bone screw includes inserting the screw first through the screw hole in the near cortex and then into the screw-receiving hole, such that rotation of the screw advances it in a direction from the near cortex of the patient's bone towards the far cortex and the bone screw engages with the screw hole in the far cortex.

35. The method of claim 33 further comprising:

providing an orthopaedic implant having an intraosseous portion having at least one screw-receiving hole; and drilling a screw hole in the near cortex of the bone, with no corresponding coaxial hole in the second cortex of the bone, the hole being generally aligned with the screw-receiving hole in the intraosseous portion;

wherein the step of inserting the bone screw includes inserting the screw first through the screw hole in the near cortex and then into the screw-receiving hole, such that rotation of the screw advances it in a direction from the near cortex of the patient's bone towards the far cortex.

36. The method of claim 35 further comprising:

providing a bone screw having an externally-threaded front end and an externally-threaded head;

wherein when the anchorage screw is inserted first through the screw hole in the near cortex and then into the screw-receiving hole, the threads of the front end of the screw engage with the threaded section of the screw-receiving hole before the threads of the head engage the near cortex.

37. The method of claim 35 further comprising:

providing a bone screw having an externally-threaded front end, an externally-threaded head, a conically-tapered intermediate screw portion which tapers from a major diameter near the head to a minor diameter towards the front end, and a transition portion between the intermediate screw portion and the head, the transition portion being provided with self-cutting flutes;

wherein when the anchorage screw is inserted first through the screw hole in the near cortex and then into the screw-receiving hole, the threads of the front end of the screw engage with the threaded section of the screw-receiving hole before the self-cutting flutes of the transition portion of the screw engage the near cortex.

38. The method of claim 35 further comprising:

providing a guide which locks to the implant and has a guide hole generally coaxial with the screw hole in the intraosseous portion when the guide is locked to the implant; and using the guide hole in the guide to drill a screw hole in the near cortex of the patient's bone.

39. An improved method for implanting a femoral component of a hip joint prosthesis, using screws rather than cement, in the intramedullary canal of the patient's femur, the femoral component having an intramedullary stem, the improvement comprising:

inserting the intramedullary stem of the femoral component into the intramedullary canal of the patient's femur; and inserting a bone screw first through the medial cortex of the femur and then into the stem, such that the front end of the screw engages with the stem of the implant and the head of the screw engages with the medial cortex, coupling the femoral component to the femur in close apposition to the interior surface of the medial cortex.

40. The method of claim 39 further comprising:

providing a femoral component of a hip joint prosthesis, the femoral component having an intramedullary stem having at least one screw-receiving hole; and drilling a screw hole in the medial cortex of the bone, with no corresponding coaxial hole in the lateral cortex of the bone, the hole being generally aligned with the screw-receiving hole in the stem;

wherein the step of inserting the bone screw includes inserting the screw first through the screw hole in the medial cortex and then into the screw-receiving hole, such that rotation of the screw advances it in a direction from the medial cortex of the patient's bone towards the lateral cortex.

41. The method of claim 39 further comprising:

providing a bone screw having an externally-threaded front end and an externally-threaded head;

wherein when the anchorage screw is inserted first through the screw hole in the medial cortex and then into the screw-receiving hole, the threads of the front end of the screw engage with the threaded section of the screw-receiving hole before the threads of the head engage the medial cortex.

42. The method of claim 39 further comprising:

providing a bone screw having an externally-threaded front end, an externally-threaded head, a conically-tapered intermediate screw portion which tapers from a major diameter near the head to a minor diameter towards the front end, and a transition portion between the intermediate portion and the head, the transition portion being provided with self-cutting flutes;

wherein when the anchorage screw is inserted first through the screw hole in the medial cortex and then into the screw-receiving hole, the threads of the front end of the screw engage with the threaded section of the screw-receiving hole before the self-cutting flutes of the transition portion engage the medial cortex.

43. The method of claim 39 further comprising:

providing a guide which locks to the femoral component and has a guide hole generally coaxial with the screw hole in the stem when the guide is locked to the femoral component; and using the guide hole in the guide to drill a screw hole in the medial cortex of the patient's femur.

44. The hip joint prosthesis of claim 21, wherein a single size of the intramedullary stem is suitable for use with a wide range of femur sizes.

45. The method of claim 39, further comprising:

providing a femoral component having a stem of one size to fit a wide range of femur sizes.

* * * * *